(12) United States Patent
Plants

(10) Patent No.: US 6,496,887 B1
(45) Date of Patent: Dec. 17, 2002

(54) SRAM BUS ARCHITECTURE AND INTERCONNECT TO AN FPGA

(75) Inventor: William C. Plants, Santa Clara, CA (US)

(73) Assignee: Actel Corporation, Sunnyvale, CA (US)

( * ) Notice: Subject to any disclaimer, the term of this patent is extended or adjusted under 35 U.S.C. 154(b) by 0 days.

(21) Appl. No.: 09/512,133

(22) Filed: Feb. 23, 2000

Related U.S. Application Data

(63) Continuation of application No. 09/039,923, filed on Mar. 16, 1998, now Pat. No. 6,038,627.
(60) Provisional application No. 60/119,574, filed on Feb. 10, 1999.

(51) Int. Cl.[7] .............................................. G06F 13/00
(52) U.S. Cl. ................... 710/100; 710/305; 710/316; 326/37; 326/38; 326/39; 326/40; 365/185.01; 365/185.08; 365/185.11
(58) Field of Search ........................... 710/100, 104, 710/305, 306, 313, 316, 317; 326/39, 37, 40, 38, 41; 365/185.01, 185.08, 185.11

(56) References Cited

U.S. PATENT DOCUMENTS 6,038,627 A * 3/2000 Plants ........................ 710/305
6,329,839 B1 * 12/2001 Pani et al. ..................... 326/41

* cited by examiner

Primary Examiner—Ario Etienne
(74) Attorney, Agent, or Firm—Sierra Patent Group, Ltd.

(57) ABSTRACT

An SRAM bus architecture includes pass-through interconnect conductors. Each of the pass-through interconnect conductors is connected to routing channels of the general interconnect architecture of the FPGA through an element which includes a pass transistor connected in parallel with a tri-state buffer. The pass transistors and tri-state buffers are controlled by configuration SRAM bits. Some of the pass-through interconnect conductors are connected by programmable elements to the address, data and control signal lines of the SRAM blocks, while other pass through the SRAM blocks with out being further connected to the SRAM bussing architecture.

5 Claims, 6 Drawing Sheets

SRAM BUS ARCHITECTURE AND INTERCONNECT TO AN FPGA

The present application is a continuation of U.S. patent application Ser. No. 09/039,923, now U.S. Pat. No. 6,038,627, entitled "SRAM BUS ARCHITECTURE AND INTERCONNECT TO AN FPGA", filed on Mar. 16, 1998 and issued on Mar. 14, 2000 which claims the benefit of provisional application Ser. No. 60/119,574 filed Feb. 10, 1999.

BACKGROUND OF THE INVENTION

1. Field of the Invention

The present invention is related to a field programmable gate array (FPGA) having embedded static random access memory for the embedded SRAM, and the connection of the SRAM bus architecture to the general interconnect architecture of the FPGA.

2. The Prior Art

As integrated circuit technology advances, geometries shrink, performance improves, and densities increase. This trend makes the design of systems of ever increasing complexity at ever decreasing cost feasible. This is especially true in logic products such as Application Specific Integrated Circuits (ASICs), Complex Programmable Logic Devices (CPLDs), and Field Programmable Gate Arrays (FPGAs).

The need for integrating fast, flexible, inexpensive memory into these logic products to provide memory for a variety of purposes such as register files, FIFOs, scratch pads, look-up tables, etc. has become more apparent, because there are significant cost and performance savings to be obtained by integrating this functionality directly into, for example, an FPGA. However, providing this memory by having other than explicitly dedicated SRAM blocks included in the FPGA has not proved satisfactory. Typically, the implementation of memory without dedicated SRAM blocks in an FPGA has been done by either providing external SRAM to the FPGA or by using the logic modules, flip-flops and interconnect of the FPGA. Both of these solutions are less than satisfactory.

Using external SRAMs with FPGA designs is undesirable for several reasons. Separate memory chips are expensive, require additional printed circuit board space, and consume I/O pins on the FPGA itself. Also, a separate memory chip is required to implement each memory function, thereby further increasing the cost.

When SRAM is implemented with the logic modules in the FPGA, it requires a substantial amount of the routing and logic resources of the FPGA, because the available logic blocks are implemented as gates and latches and the programmable interconnect is employed to connect them. This substantially degrades both the performance and flexibility of the FPGA by consuming a considerable amount of logic array resources, and imposes critical paths that are quite long for even a small memory block.

Xilinx offers the capability of using the configurable logic blocks on their 4000 Series of parts as 16×1 SRAM blocks, but requires the use of normal interconnect to combine the blocks into larger memory configurations. While this distributed SRAM approach is an improvement in density and is flexible for building larger memories, it is still slow and consumes logic array resources. The necessary overhead circuitry was sufficiently large that Xilinx actually removed it when they developed their low cost 4000-D parts. On their 4000-E Series parts, they offer the ability to configure two configurable logic blocks to emulate a dual ported 16×1 SRAM block, however, this design still carries with it performance and flexibility degradation.

Altera has also attempted to improve on the connection of the SRAM blocks in their embedded array blocks for their 10K FLEX parts. They include one or more columns on their larger parts of embedded array blocks which are size matched to their logic array blocks. The embedded array blocks contain 2K bits of single ported SRAM configurable as 256×8, 512×4, 1024×2, or 2048×1. This approach builds the flexibility of different widths and depths into the SRAM block, but at a significant performance cost since the access time of an embedded array block is very slow for a memory of the size and the technology in which it is built. Further, array routing resources are required for memory configurations other than those indicated.

Another approach to SRAM memory in FPGA applications is found in "Architecture of Centralized Field-Configurable Memory", Steven J. E. Wilton, et. al., from the minutes of the 1995 FPGA Symposium, p. 97. This approach involves a large centralized memory which can be incorporated into an FPGA. The centralized memory comprises several SRAM arrays which have programmable local routing interconnect which are used exclusively by the centralized memory block. The local routing interconnects are used to make efficient the configuration of the SRAMs within the centralized memory block. However, the local interconnect structure disclosed in Wilton suffers performance problems due to excessive flexibility in the interconnect architecture.

Actel's 3200 DX family of parts attempted an intermediate approach by including columns of dual ported SRAM blocks with 256 bits which are configurable as either 32×8 or 64×4. These blocks are distributed over several rows of logic modules to match the density of I/O signals to the SRAM block to that of the surrounding FPGA array. Polarity control circuits were added to the block enable signals to facilitate use as higher address bits. This architecture was designed to provide high performance and reasonable flexibility, with density approaching the inherent SRAM density of the semiconductor process, and routing density comparable to the rest of the logic array. Unfortunately, this approach required array routing resources to interconnect SRAM blocks into deeper and wider configurations.

One of the desirable attributes of user-assignable SRAM blocks in an FPGA architecture is the ability to connect the SRAM blocks to one another to form memories that are either wider (i.e. longer word length) or are deeper (i.e. more words). In connecting SRAM blocks into deeper and wider configurations it must be appreciated that the addresses have to go to each of the SRAM blocks, the write data has to go to each of the SRAM blocks, and the data must be able to be read from all of the SRAM blocks. In addition, the control signals used by the SRAM blocks to read and write data must also be routed to each of the SRAM blocks.

Since routing resources must be used to connect the dedicated SRAM blocks to one another to create either wider or deeper memories, and given that routing resources are not unlimited, preventing a degradation in the performance of the FPGA by efficiently forming deeper and wider memories is an important concern. In preventing a degradation of the FPGA performance, the connection to the user of SRAM blocks to provide deeper and wider memory configurations should not substantially impact the place and route algorithms of the FPGA, nor prevent the use of place and route algorithms for connecting the logic in the FPGA. Several approaches are known in the art for configuring dedicated SRAM blocks to provide deeper and wider memories.

The difficulty in creating deeper and wider SRAM block configurations in the prior art has been that array routing resources have been required to interconnect the SRAM blocks into these configurations. Part of the problem has been that the array routing resources have not been used very efficiently. In certain instances, this was due to the fact that the devices to which the SRAM blocks have been added were not originally designed with embedded SRAM blocks, rather the SRAM blocks have been inserted as an add-on piece.

These problems are better illustrated with reference to FIGS. 1 and 2. In FIG. 1, four 256×8 SRAM blocks are connected into a deeper configuration or essentially a 1024×8 memory. In this configuration it can be seen that the lower order write address bits must be supplied to each of the 256×8 SRAM blocks along with the write data. Additionally, logic must be implemented to provide a 2 to 4 decode of the two higher order address bits used to select the one of four 256×8 SRAM blocks to which the data will actually be written. To read data from the SRAM blocks in this deeper configuration, the lower order read address bits must be supplied to each of the 256×8 SRAM blocks, and then additional logic must be implemented to provide a 4 to 1 multiplexer so that the correct data may be selected from the 1 of 4 SRAM blocks from which data is being output.

In FIG. 2, four 256×8 SRAM blocks are configured in a wider configuration to provide a 256×32 SRAM block. In this configuration, the write address must be supplied to each of the 256×8 blocks to perform a write operation, and to perform a read operation the read address must also be supplied to each of the 256×8 blocks. The write data must be routed so that the first 8 bits of the data at a particular address location is supplied to a first 256×8 SRAM block, the next 8 bits of the data at that particular address location is supplied to a second 256×8 SRAM block, and the third and fourth 8 bits of data at the same address are supplied to a third and fourth SRAM block, respectively. For a data read, the output of the SRAM blocks must be connected so that the correct 8 bits are taken from each of the four 256×8 SRAM blocks to form a single 32 bit word.

Clearly there is a need for a flexible SRAM bus architecture in an FPGA for embedding user-assignable SRAM blocks into the FPGA. The SRAM bus architecture of the present invention provides routing resources for efficiently using individual SRAM blocks or for connecting multiple blocks of user SRAM to make wider and/or deeper memory configurations. The SRAM bus architecture of the present invention is implemented with minimal use of the routing resources of the array, and with a minimal degradation in the performance of the FPGA.

BRIEF DESCRIPTION OF THE INVENTION

According to the present invention, an SRAM bus architecture is disclosed that is suitable for use with a plurality of embedded SRAM blocks in an FPGA. The SRAM bus architecture is employed to connect the SRAM blocks in a group together into deeper and wider configurations without employing the general interconnect architecture resources of the FPGA, and to connect the SRAM blocks to the logic modules in an FPGA The SRAM bus architecture includes pass-through interconnect conductors. Each of the pass-through interconnect conductors is connected to the routing channels of the general interconnect architecture of the FPGA through an element which includes a pass transistor connected in parallel with a tri-state buffer. The pass transistors and tri-state buffers are controlled by configuration SRAM bits. Some of the pass-through interconnect conductors are connected by programmable elements to the address, data and control signal lines of the SRAM blocks, while other pass through the SRAM blocks with out being further connected to the SRAM bussing architecture. This aspect of the present invention, increases the efficiency of the place and route of the FPGA.

The SRAM blocks are dual ported (simultaneous read/write), and include an additional load port that interacts with the circuitry employed in the loading and testing of the configuration data of the FPGA core. Each SRAM block contains circuits in both the read port and the write port that together with the SRAM bus architecture permit the SRAM blocks to be connected into deeper and wider configurations by without any additional logic as required by the prior art.

In the preferred embodiment, there eight fully independent blocks of 2K bit SRAM blocks, wherein each SRAM block is organized as 256 words of 8 bits each. The eight SRAM blocks are further divided into two groups such that the SRAM blocks in each of the groups are substantially contiguous to the extent that the address busses, data busses, and control signal lines of each of the user-configurable SRAM blocks in a group can be commonly connected by user-programmable elements at their edges to facilitate directly combining the user-configurable SRAM blocks in a group into wider and/or deeper user-assignable memory configurations.

DETAILED DESCRIPTION OF A PREFERRED EMBODIMENT

Those of ordinary skill in the art will realize that the following description of the present invention is illustrative only and not in any way limiting. Other embodiments of the invention will readily suggest themselves to such skilled persons.

In the present invention, the SRAM bus architecture associated with the SRAM blocks is distinct from the general interconnect architecture of the FPGA. As will be described below, a distinct SRAM bus architecture provides advantages in connecting the SRAM blocks to the other portions of the FPGA not contemplated by the prior art. The SRAM bus architecture of the present invention does not require the use of the routing resources of the general interconnect architecture of the FPGA to connect SRAM blocks together in the manner known in the prior art, and can make use of the overhead generally allocated in SRAM blocks for the formation of address busses, data busses, and control lines.

Figure 1:
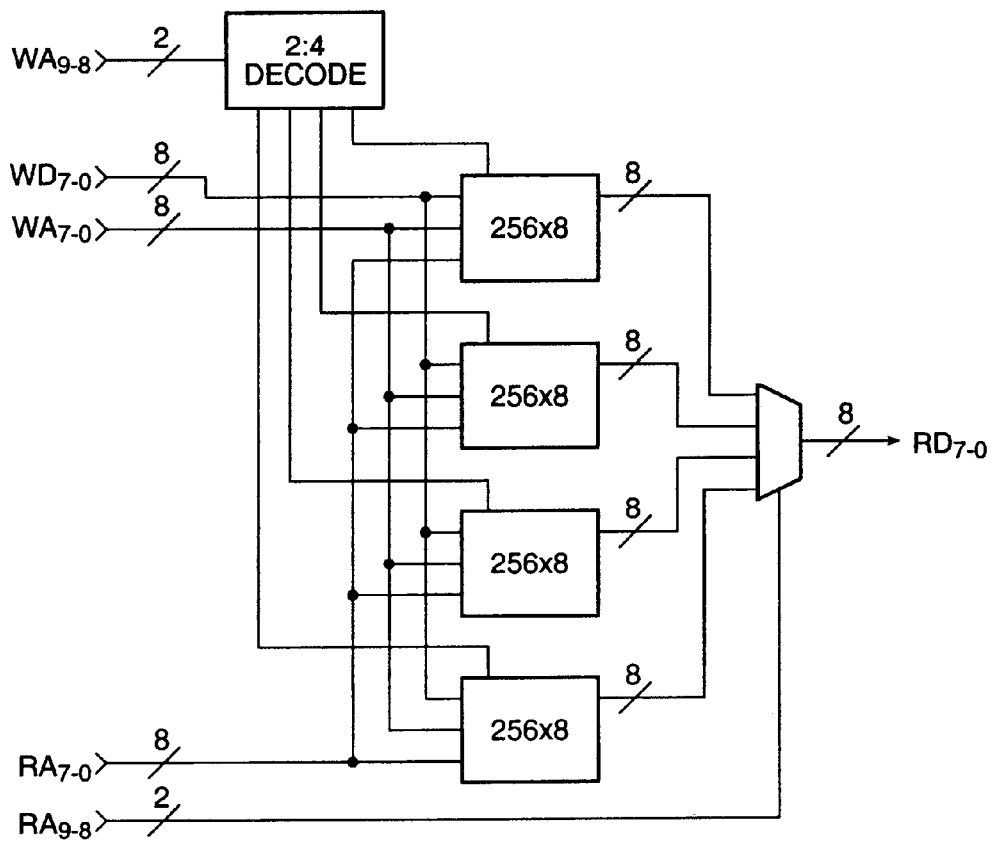
FIG. 1 illustrates the connection of four 256×8 SRAM blocks into a deeper memory configuration according to the prior art.
Figure 2:
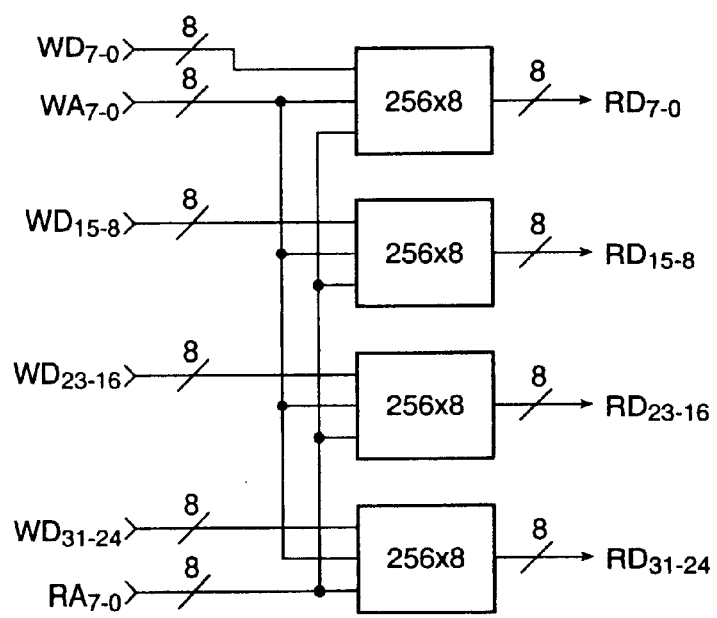
FIG. 2 illustrates the connection of four 256×8 SRAM blocks into a wider memory configuration according to the prior art.
Figure 3:
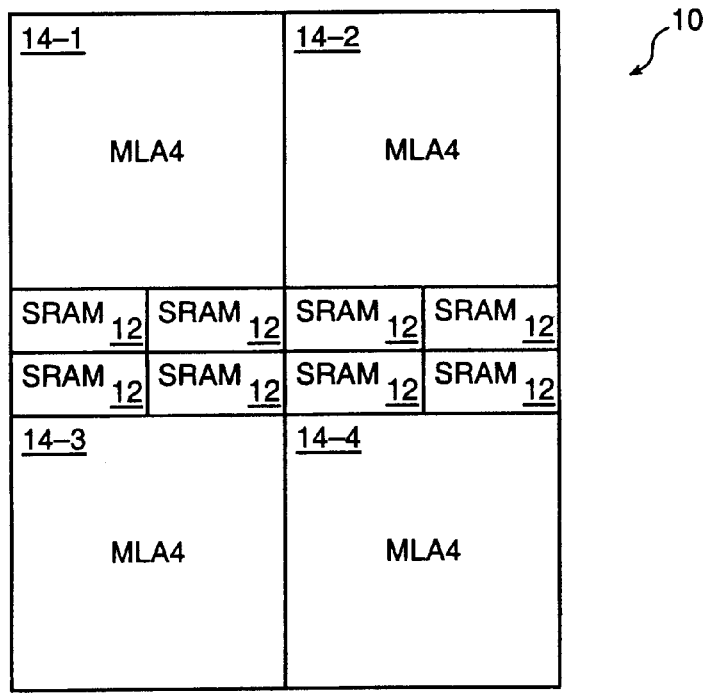
FIG. 3 illustrates in block diagram an SRAM based FPGA core according to the present invention.

Turning now to FIG. 3, a block diagram of the FPGA core 10 in a flexible, high-performance SRAM based FPGA architecture having user-assignable SRAM blocks 12 according to the present invention is illustrated. The FPGA core 10 includes a plurality of logic function modules disposed within a multi-level architecture (MLA) of routing resources. The blocks 14-1 through 14-4 in FPGA core 10 illustrate a grouping of logic modules in the MLA termed MLA4. In the preferred embodiment, there are approximately 50K gates combined in blocks 14-1 through 14-4. The SRAM blocks 12 comprise 16K bits of user-assignable SRAM divided into eight dedicated blocks of 2K bits. The user-assignable SRAM blocks 12 will be more fully described below.

Figure 4:
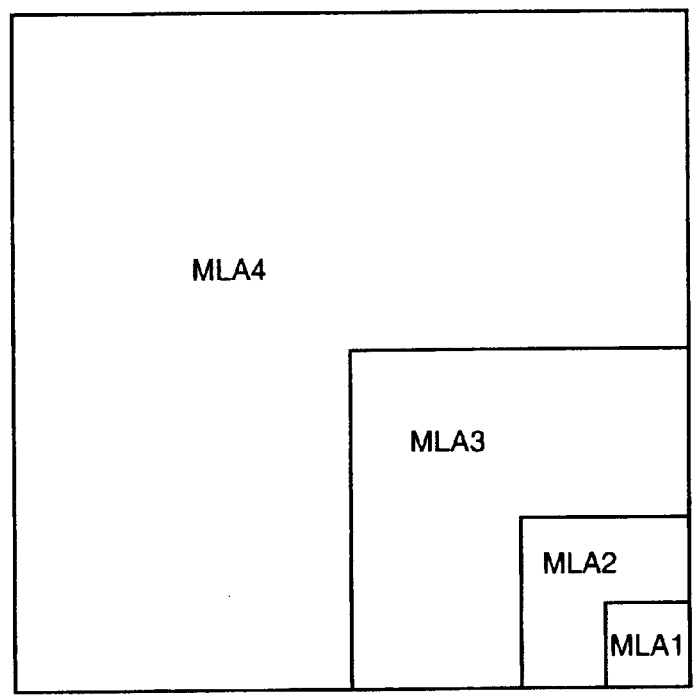
FIG. 4 illustrates a hierarchical embodiment of groups of logic modules according to the present invention.

Depicted in FIG. 4, are the relative number of logic modules included in each of the routing resource levels MLA1, MLA2, MLA3, and MLA4 in the MLA. In the grouping of logic modules in the MLA, each level in the MLA includes four groups of logic modules from the next lower level in the MLA. The highest level in the MLA is MLA5 comprising all of the logic modules in the FPGA core 10, the SRAM blocks 14, the configuration SRAM, and other circuits in the FPGA.

Figure 5:
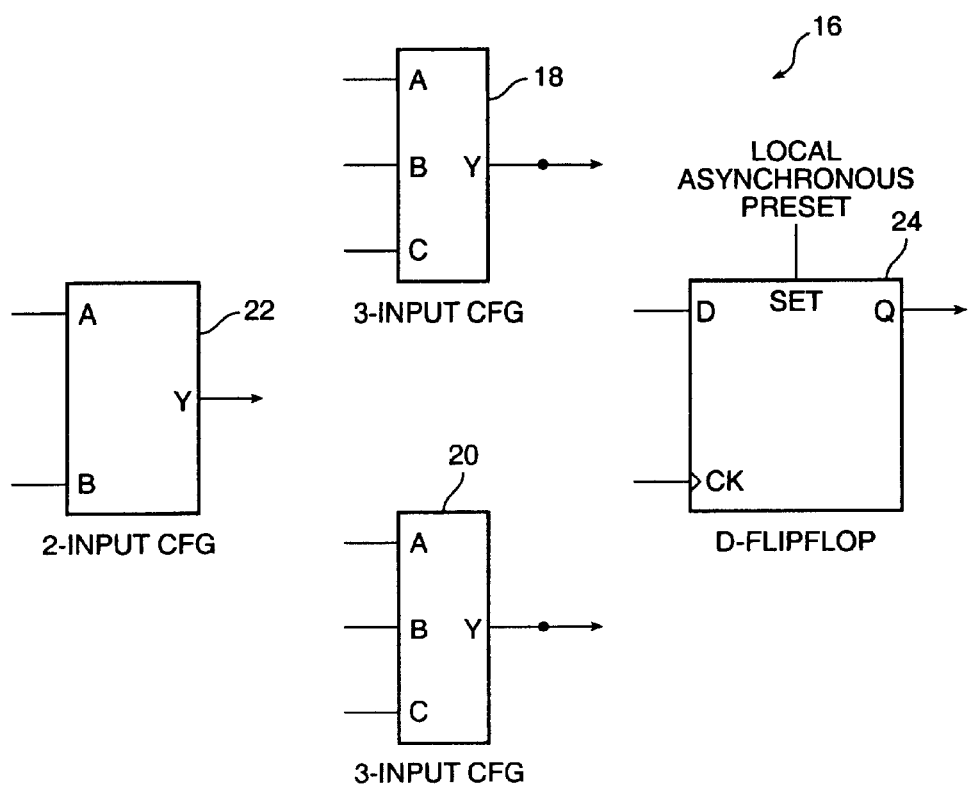
FIG. 5 illustrates in block diagram the logic entities included in a logic module suitable for use according to the present invention.

The smallest grouping of logic modules is a level MLA1 in the MLA. Each MLA1 level includes four blocks each having four clusters. Each of the clusters can be considered as a logic module having four separate logic entities. FIG. 5 illustrates the logic included in a cluster 16. The cluster 16 includes first and second three-input configurable function generators (CFG) 18 and 20, respectively, a two-input CFG 22, and a D-type flip-flop 24. With a three input CFG any three input boolean logic function may be implemented, and with a two input CFG any two input boolean logic function may be implemented. To avoid overcomplicating the disclosure and thereby obscuring the present invention, many of the details of the entire MLA are not disclosed herein.

Referring again to FIG. 3, each user-assignable SRAM block 12 includes 256 words of 8 bits, and each user-assignable SRAM block 12 is fully independent from the other SRAM blocks 12. The eight bits of addressing for each word in an SRAM block 12, and the eight bit word length are convenient for connection to the MAL4 blocks 141 through 14-4. It will be appreciated by persons of ordinary skill in the art that SRAM blocks 12 which are either larger or smaller than 2k bits may be utilized, and further that either fewer or greater than eight SRAM blocks 12 may be employed. The number of words in an SRAM block 12, the length of a word in an SRAM block 12, the number of bits in an SRAM block 12, and the number of SRAM blocks 12 are a matter of design choice.

In the FPGA core 10, the SRAM blocks 12 are preferably split into two groups of four SRAM blocks 12. It should be appreciated that the number of SRAM blocks in a group is a matter of design choice. A first group of four SRAM blocks 12 is disposed between MLA4 blocks 14-1 and 14-3, and a second group of four SRAM blocks 12 is disposed between MLA4 blocks 14-2 and 14-4. The SRAM blocks 12 in each of the groups are substantially contiguous to the extent that the address busses, data busses, and control signal lines of each of the SRAM blocks 12 in a group can be commonly connected to facilitate directly combining the SRAM blocks 12 in a group into wider and/or deeper user-assignable memory configurations. Further, the two groups can be connected together, if desired, through the logic modules and the general interconnect resources of the MLA.

Figure 6:
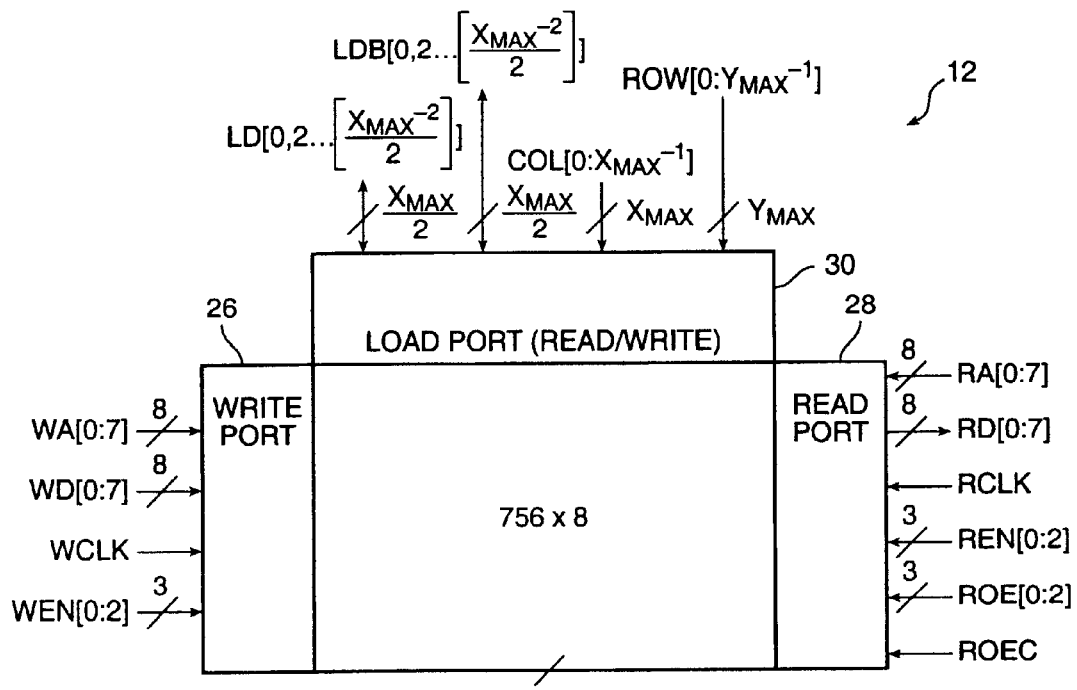
FIG. 6 illustrates block diagram an SRAM block depicting a write port, read port and load port suitable for use according to the present invention.

Referring now to FIG. 6, each SRAM block 12 is depicted as dual ported SRAM having write and read ports 26 and 28, respectively. Connected to write port 26 are an eight-bit write address (WA) bus, an eight-bit write data (WD) bus, a write clock (WCLK) input, and a three-bit write enable (WEN) bus. Connected to the read port 22 are an eight-bit read address (RA) bus, an eight-bit read data (RD) bus, a read clock (RCLK) input, a three-bit read enable (REN) bus, a three-bit read output enable (ROE) bus, and read output enable control (ROEC) input. Each of the control signal lines, namely, WCLK, WEN, RCLK, REN, ROE, ROEC, have a well known in-line inverter, comprising an XNOR gate and a polarity control bit as is well known in the art and as is described below with respect to FIG. 10, that may be selected to provide a connected signal or its complement.

To avoid over complicating the present disclosure and obscuring the present invention only some of the details of the SRAM blocks 12 will be disclosed herein. A more detailed description of the SRAM blocks 12 are disclosed in co-pending application Ser. No. 09/039,891, filed Mar. 16, 1998, (Entitled "EMBEDDED STATIC RANDOM ACCESS MEMORY FOR FIELD PROGRAMMABLE GATE ARRAY", by inventors William C. Plants, Anthony Bell, and Jim Joseph, and filed the same day as this application, and assigned to the assignee of the present invention and specifically incorporated herein by reference.

Also depicted in FIG. 6 is a load port 30 having connected thereto a column address bus, a row address bus, a LD line, and a LDB line. The load port 30 is controlled by the circuitry employed to load the configuration data into the configuration SRAM of the FPGA core 10. To avoid over complicating the present disclosure and obscuring the present invention, the details of the circuitry employed in the loading and testing of the configuration data of the FPGA core 10 will not be disclosed herein. These details are disclosed in co-pending application Ser. No. 09/039,924, filed Mar. 16, 1998, (Entitled "CYCLIC REDUNDANCY CHECKING OF A FIELD PROGRAMMABLE GATE ARRAY HAVING AN SRAM MEMORY ARCHITECTURE", by inventor William C. Plants, and filed the same day as this application, and assigned to the assignee of the present invention and specifically incorporated herein by reference.

Figure 7:
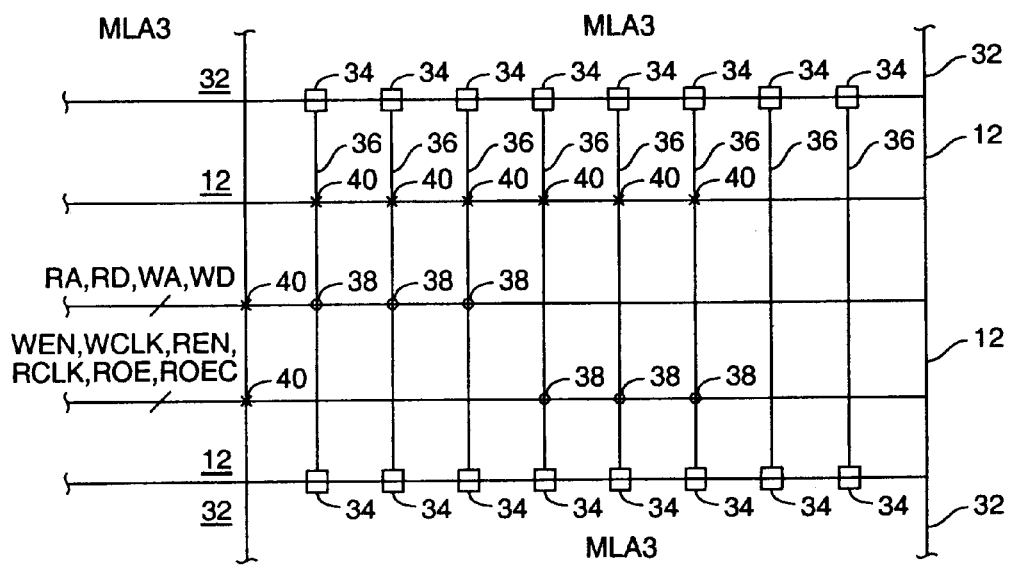
FIG. 7 is a schematic diagram of the connection of the interconnect architecture of an MLA3 to the SRAM bus architecture according to the present invention.

Referring now to FIG. 7, a more detailed block diagram of a portion of the FPGA core 10 depicts the interconnectivity between the SRAM block bus architecture and the routing channels of an MLA3 32. In FIG. 7, connectors 34 between an MLA3 32 and the SRAM blocks 12 are disposed on the edge of an MLA3 32 adjacent an SRAM block 12. Each of the connectors 34 represents a plurality of user-programmable interconnect elements disposed between the conductors of a routing channel in an MLA3 32 and a plurality of pass-through interconnect conductors 36 spanning the SRAM block 12.

It is presently contemplated that each MLA4 14 will have sixteen connectors 34 on the edge abutting SRAM blocks 12. As depicted in FIG. 3, the width of an MLA4 14 is such that two SRAM blocks 12 will fit along the side of an MLA4 14. Accordingly, eight connectors 34 in an MLA3 32 will abut each SRAM block 12 as illustrated in FIG. 7. Of these eight connectors 34, some are employed to make selective connections to pass-through interconnect conductors 36 that are not further connectable to the SRAM bussing architecture, while the remaining block connectors 34 are employed to make selective connections to pass-through interconnect conductors 36 that are further connectable to the SRAM bussing architecture.

Figure 8A:
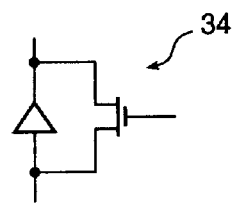
FIGS. 8A–8C illustrate programmable connections according to the present invention.

Selective connections are made between the interconnect conductors in the routing channels of the MLA3 32 and the pass-through interconnect conductors 36 by the user-programmable interconnect conductors of the connectors 34. The user programmable interconnect elements of the connectors 34 is preferably a pass transistor connected in parallel with a tri-state buffer as illustrated in FIG. 8A.

Figure 8B:
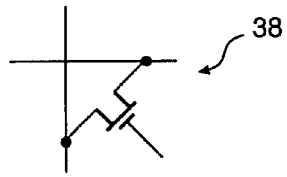

The WA, WD, WCLK, WEN, RA, RD, RCLK, REN, ROE, and ROEC signal lines of the SRAM bus architecture all horizontally traverse each of the SRAM blocks 12 to form intersections with the pass-through interconnect conductors 36. The address, data and control lines and are selectively connectable by user-programmable interconnect elements 38 to the pass-through interconnect conductors 36. The user-programmable interconnect elements 38 are preferably pass gates controlled by SRAM configuration bits disposed between the address, data and control lines and the pass-through interconnect conductors 36 in a manner depicted in FIG. 8B. Those of ordinary skill in the art will appreciate that the programmable elements may also include other programmable elements known in the art, further including, antifuses, E²PROM bits, etc.

The intersections of the address, data and control signal lines in the SRAM bus architecture with the pass-through interconnect conductors 36 may be less than fully populated with user-programmable interconnect elements 38. As illustrated in FIG. 7, user-programmable interconnect elements 38 are disposed at the intersections of the address and data lines and a first group of pass-through interconnect conductors 36, and user-programmable interconnect elements 38 are also disposed at the intersections of the control signal lines and a second group of pass through interconnect conductors 36. It should be appreciated that any of the pass through interconnect conductors 36 may form intersections with both address and data lines and also control signal lines at which are disposed user-programmable interconnect elements 38. It will be appreciated that the intersections of the address, data and control signal lines and the pass-through interconnect conductors 36 at which are disposed the user-programmable interconnect elements 38 is a matter of design choice.

Figure 8C:
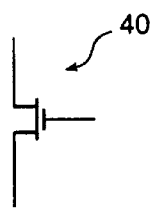

In FIG. 7, user-programmable interconnect elements 40, which are preferably pass transistors, are disposed in series with the pass-through interconnect conductors 36 at the edges of the SRAM blocks 12, and also in series with the address, data and control signal lines at the edge of two SRAM blocks 12 in the same group. A pass transistor disposed in series with two conductors is illustrated in FIG. 8C.

Figure 9:
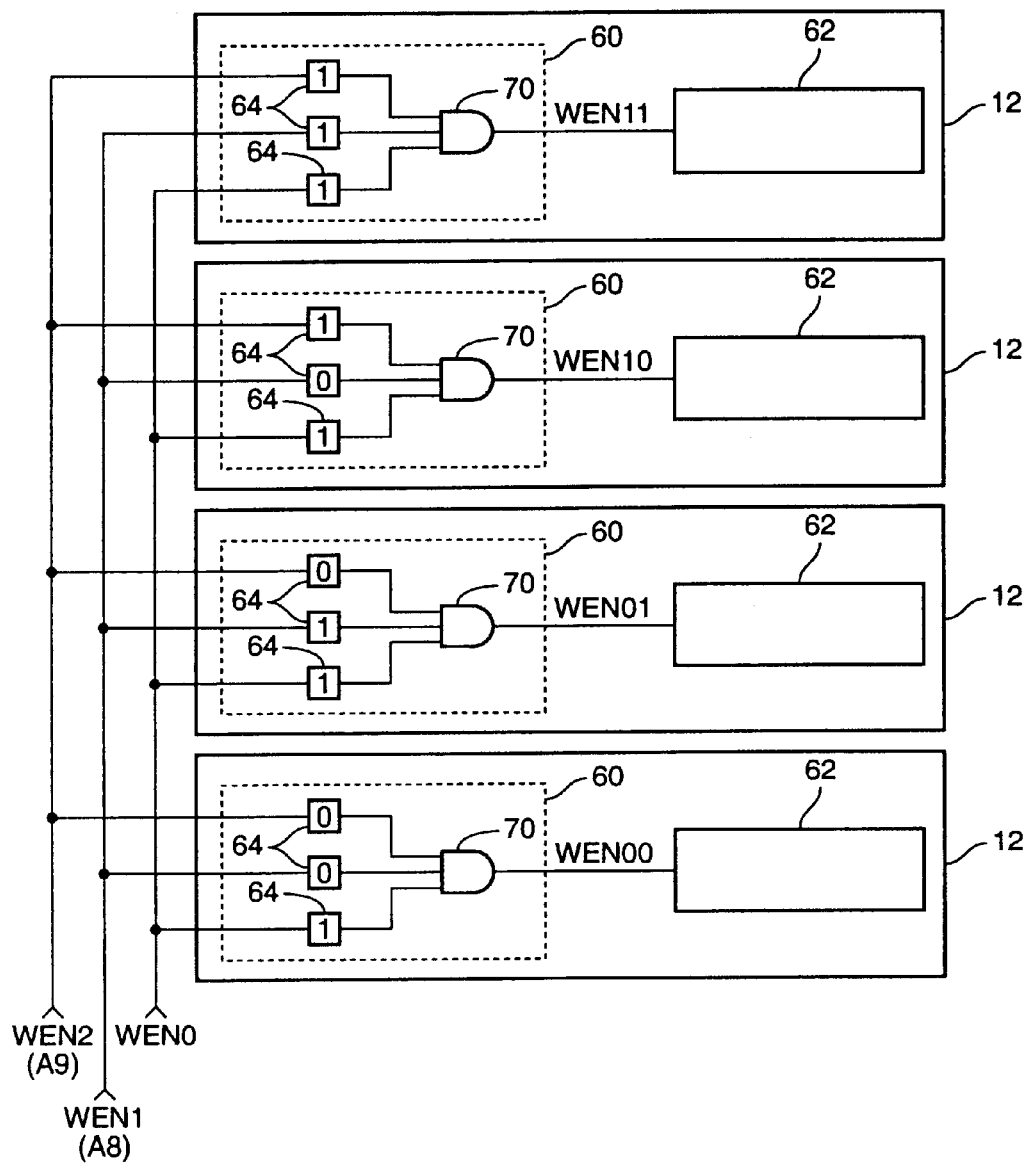
FIG. 9 is a circuit diagram illustrating the enable logic in the write port of the SRAM blocks according to the present invention.
Figure 10:
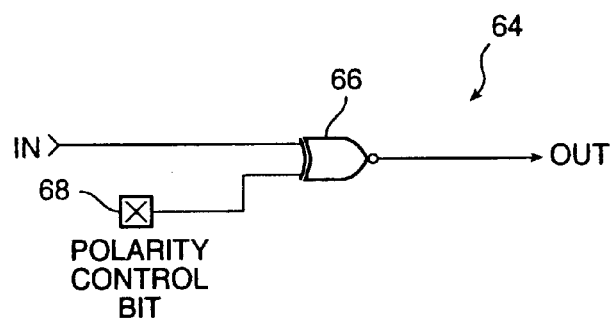
FIG. 10 illustrates a polarity select circuit suitable for use in the present invention.
Figure 11:
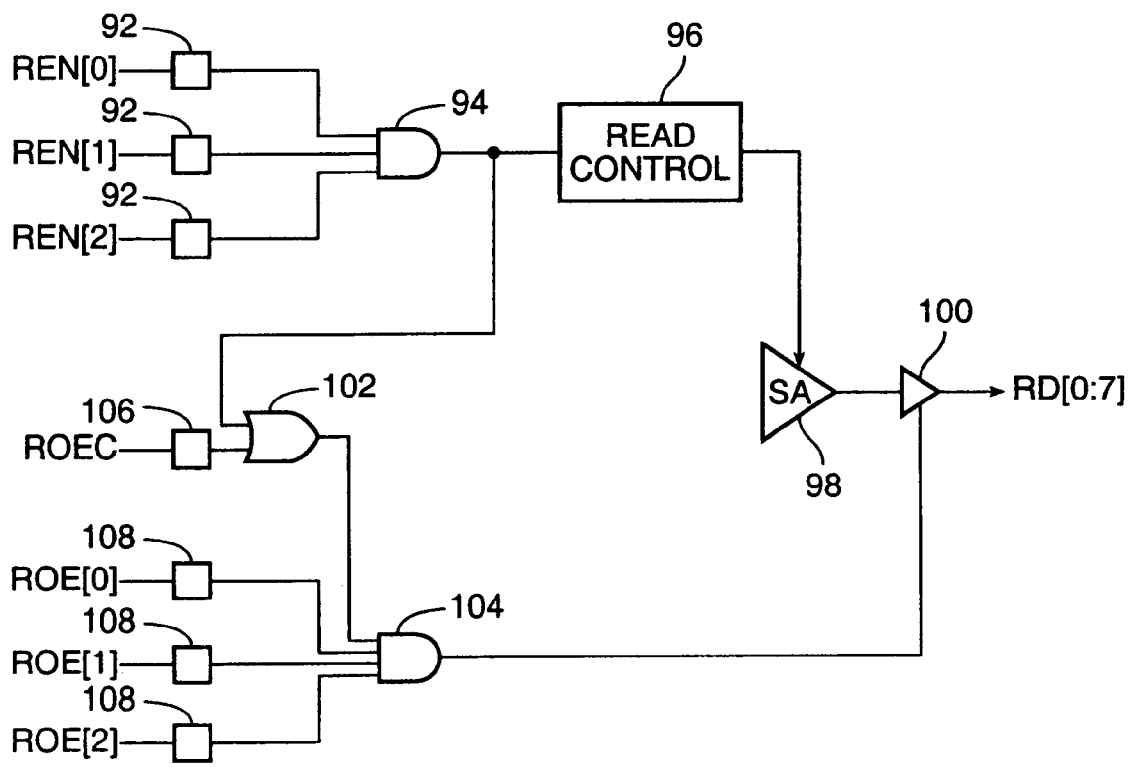
FIG. 11 illustrates high impedance and fast access output features of the read port in each of the SRAM blocks according to the present invention.

According to the present invention, each SRAM block 12, contains circuits in both the read port and the write port that together with the SRAM bus architecture disclosed herein permit the SRAM blocks 12 to be connected into deeper and wider configurations by without any additional logic as required by the prior art. Referring now to FIGS. 9, 10, and 11 the portions of the SRAM blocks 12 to which the control lines and high impedance controls employed to connect SRAM blocks 12 into wider and deeper configurations are shown in greater detail.

In FIG. 9, four SRAM blocks 12 in a group are illustrated. The enable logic 60 in the write port 26 of each of the SRAM blocks 12 to which is connected the WEN control signals has been separated from the remaining portions 62 of the SRAM blocks 12 to better illustrate the manner in which the SRAM blocks 12 may be connected into deeper and wider configurations. Connected to each of the SRAM blocks 12 are three WEN control signals representing the eighth and ninth bits of a write address, and a write enable signal. In each of the SRAM blocks 12, the three WEN control lines are connected to polarity select circuits 64.

In the preferred embodiment of the present invention, each of the polarity select circuits 64 comprises an exclusive NOR (XNOR) gate 66 and a polarity control bit 68 as illustrated in FIG. 10. The operation of the exclusive XNOR gate 64 is well understood by those of ordinary skill in the art. Depending upon the value of the polarity control bit 68, the input to the exclusive XNOR gate 66 can either be passed through the exclusive XNOR gate 66 or complimented. The polarity control bit 68 is provided as part of the configuration memory.

In each of the SRAM blocks 12, the AND gates 70 connected to the outputs of the polarity select circuits 64 form an AND decode of the WEN1 and WEN2 signals (the eighth and ninth address bits) as is well understood by those of ordinary skill in the art. The output of each of the AND gates 70 provides a write enable signal to the remainder of each of the SRAM blocks 62.

Turning now to FIG. 11, a simplified schematic of the connections of the REN, ROE, and the ROEC to an SRAM block 12, is illustrated. In the illustrative SRAM block 12, each of three REN signals are connected to a polarity select circuit 92 similar to the polarity select circuit 64 shown in FIG. 10. The outputs from the polarity select circuits 92 are connected to the input of an AND gate 94. As is well understood by those of ordinary skill in the art, the polarity select circuits 92 and AND gate 94 form an AND decoder for the REN signals.

The output of the AND gate 94 is connected to a read control circuit 96 in the read port 28 of SRAM block 12. One of the outputs of the read control circuit 96 is connected to and controls the enable input to sense amplifiers 98. The sense amplifiers 98 are connected to the SRAM cells in the SRAM block 12. During a read operation, the sense amplifiers 98 sense the contents of the SRAM cells in the SRAM block. The output of the sense amplifiers 98 are connected to the inputs of output drivers 100. The outputs of output drivers 100 are connected to the RD bus. When desired, the output drivers 100 can be placed in a high impedance condition by the output from AND gate 94 connected through a first input of an OR gate 102 and a first input of an AND gate 104 to the enable input of the output driver 100. By including the high impedance feature for the RD bus by placing the output drivers 100 into a high impedance condition, the SRAM blocks 12 can be connected into deeper configurations without the need for external logic.

With the high impedance RD bus, a fast access mode of operation may be implemented. Since enabling the output drivers 100 is significantly faster than an SRAM read operation, providing a fast enable to the output drivers 100 when a read has previously taken place in the SRAM block 12 can create the illusion of a faster read access than is normally possible. Thus in a deep multiple SRAM block configuration, a read can be conducted in all the SRAM blocks 12 in the configuration and then deft manipulation of the output driver 100 enables can create an effectively larger output bandwidth.

In FIG. 11 fast access circuitry is illustrated wherein a second input of OR gate 102 is connected to the ROEC input through polarity select circuit 106. The output of OR gate 102 is connected to a first input of AND gate 104 having second, third and fourth inputs connected to the three-bit ROE bus through polarity select circuits 108. In the operation of the fast access mode, the ROEC input is used to force a logic-1 into the first input of the AND gate 104 so the output buffer enable is solely under the control of the ROE bus. In normal operation, the ROEC input and the ROE bus are set up so that the output of the AND gate 94 controls the output drivers 100.

In the present invention, the independence of the SRAM bus architecture associated with the SRAM blocks 12 from the FPGA interconnect architecture has several distinct advantages over the connectivity of prior art SRAM blocks to an FPGA interconnect architecture. As described above, in connecting the FPGA architecture to the SRAM bus architecture, some of the pass-through interconnect conductors 36 may be made connectable to the SRAM bus architecture, while others of the pass-through interconnect conductors 36 are not made connectable to the SRAM bus architecture.

In a first aspect, the pass-through interconnect conductors 36 not connected to the SRAM bus architecture enhance the overall part connectivity by providing connection paths between MLA4 14 that are not directly connectable to the SRAM bus architecture. This is an important aspect of the present invention, since it permits interconnection between an MLA4 14 located adjacent to one SRAM block 12 and an MLA4 14 located adjacent another SRAM block 12 as if the SRAM blocks 12 were not present, thus rendering the SRAM blocks 12 virtually transparent to the routing resource.

In a second, aspect, the pass-through interconnect conductors 36 that are selectively connectable to the SRAM bus architecture provide ample connection of the MLA4 14 to the SRAM blocks 12. Further, because FPGA routing resources are not used to route common address busses, data busses, and control lines between the SRAM blocks 12, the routing efficiency of the FPGA architecture will increase. It will be appreciated by those of ordinary skill in the art that the common address busses, data busses, and control lines in the SRAM blocks 12 require no additional integrated circuit space overhead, because space is already allocated generally for the formation of address busses, data busses, and control lines in SRAM blocks.

The FPGA architecture described herein offers flexible, high-performance SRAM to the user of FPGAs. The flexibility of the architecture permits efficient implementation of on-chip data storage, register files, and FIFOs. Small-capacity high-speed dual-port SRAM can be used to handle ATM data packets; for DRAM and DMA control; as a "rubber-band" synchronizer between two clocks of differing frequency; and as a coefficient table for FIR and IIR filters (wherein many integer coefficients are stored once and retrieved repeatedly).

By offering many independent blocks, the FPGA can support many different sorts of applications. Unused blocks can be turned into 8-bit registers. On-chip SRAM is many times more efficient for storing data than logic modules and saves many valuable I/O pins. Thus, the user can fit more logic into, and obtain greater performance from, a given FPGA.

Those of ordinary skill in the art will recognize that the SRAM architecture disclosed herein can also be utilized for FIFO, ROM, and as single port RAM with or without employing a bidirectional data bus.

While embodiments and applications of this invention have been shown and described, it would be apparent to those skilled in the art that many more modifications than mentioned above are possible without departing from the inventive concepts herein. The invention, therefore, is not to be restricted except in the spirit of the appended claims.

What is claimed is:

1. A component architecture for a plurality of dedicated SRAM blocks associated with a plurality of multi-level architecture groupings of logic modules (MLA) in an FPGA comprising:

a first column and a second column adjacent to said first column wherein each of said first and second columns comprises:
a first MLA,
a first SRAM block,
a second SRAM block,
a second MLA,
a plurality of pass-through interconnector conductors vertically spanning each of said first and second SRAM blocks,
SRAM address, data and control signal lines all horizontally traversing each said SRAM block and forming intersections with said plurality of pass-through interconnector conductors,
a first edge of each of said first and second SRAM blocks, wherein each said first edge is adjacent to a one of said first MLA and said second MLA,
at least two edges of each of said first and said second SRAM blocks, each said at least two edges being adjacent to another SRAM block,
a first plurality of user-programmable interconnectors of each first edge connecting conductors of a routing channel in said one MLA adjacent said first edge and said plurality of pass-through interconnector conductors, and
a second plurality of user-programmable interconnectors on each said at least two edges selectively connecting said SRAM address, data and control signal lines and said plurality of pass-through interconnector conductors spanning each of said first and said second SRAM blocks.

2. The component architecture of claim 1 comprising a third column, wherein said third column is arranged in essentially the same manner as said first column and said second column and wherein said third column is adjacent to at least one of said first column and said second column.

3. The component architecture of claim 1 wherein said first plurality of user-programmable interconnectors of each said first edge is a pass transistor connected in parallel with a tri-state buffer.

4. The component architecture of claim 1 wherein each of said first and second pluralities of user-programmable interconnectors is a pass gate controlled by SRAM configuration bits.

5. The component architecture of claim 1 wherein each of said second plurality of user-programmable interconnecters of said at least two is a pass transistor.

* * * * *